US009566398B2

(12) United States Patent
Heskamp et al.

(10) Patent No.: US 9,566,398 B2
(45) Date of Patent: Feb. 14, 2017

(54) ATOMISING BODY, ATOMISING DEVICE, INHALER, MANUFACTURING METHOD OF MANUFACTURING AN ATOMISING BODY AND ASSEMBLY METHOD FOR ASSEMBLING AN ATOMISING DEVICE

(75) Inventors: Iwan Rutger Heskamp, Enschede (NL); Wilhelmus Petrus Johannes de Kruijf, Enschede (NL); Wietze Nijdam, Enschede (NL); Jeroen Mathijn Wissink, Enschede (NL)

(73) Assignee: MEDSPRAY XMEMS B.V., Enschede (NL)

(*) Notice: Subject to any disclaimer, the term of this patent is extended or adjusted under 35 U.S.C. 154(b) by 1358 days.

(21) Appl. No.: 13/257,423

(22) PCT Filed: Apr. 22, 2010

(86) PCT No.: PCT/NL2010/000070
§ 371 (c)(1),
(2), (4) Date: Sep. 19, 2011

(87) PCT Pub. No.: WO2010/123347
PCT Pub. Date: Oct. 28, 2010

(65) Prior Publication Data
US 2012/0012105 A1 Jan. 19, 2012

(30) Foreign Application Priority Data

Apr. 23, 2009 (NL) ..................................... 2002787

(51) Int. Cl.
*A61M 11/00* (2006.01)
*A61M 11/08* (2006.01)
(Continued)

(52) U.S. Cl.
CPC .......... *A61M 11/003* (2014.02); *A61M 11/007* (2014.02); *A61M 11/08* (2013.01);
(Continued)

(58) Field of Classification Search
CPC ... A61M 11/00; A61M 11/006; A61M 11/007; A61M 11/008; A61M 11/003; A61M 11/02; A61M 11/001; A61M 11/04; A61M 15/00; A61M 15/0001; A61M 2207/00; B05B 1/00; B05B 1/14
See application file for complete search history.

(56) References Cited

U.S. PATENT DOCUMENTS 5,289,818 A * 3/1994 Citterio et al. .......... 128/200.14
6,267,251 B1 7/2001 Sullivan
(Continued)

FOREIGN PATENT DOCUMENTS

WO 0218058 A1 3/2002

*Primary Examiner* — Justine Yu
*Assistant Examiner* — Colin W Stuart
(74) *Attorney, Agent, or Firm* — Hoffmann & Baron, LLP

(57) ABSTRACT

A method of manufacturing an atomizing body for an atomizing device includes the steps of providing a support element having a first layer on a first surface of the support element and a second layer on a second surface of the support element, the first layer including a first perforated membrane and the second layer including a process orifice, etching a cavity through the support element, the cavity forming a fluid connection from the process orifice to the perforated membrane, by providing etching substance to the process orifice. The atomizing body as obtained may advantageously be applied in an atomizing device or an inhaler.

26 Claims, 9 Drawing Sheets

(51) Int. Cl.
*A61M 15/00* (2006.01)
*B01D 63/08* (2006.01)
*B01D 67/00* (2006.01)
*B05B 1/14* (2006.01)
*B65D 83/14* (2006.01)

(52) U.S. Cl.
CPC ......... *A61M 15/009* (2013.01); *B01D 63/081* (2013.01); *B01D 63/082* (2013.01); *B01D 67/0062* (2013.01); *B05B 1/14* (2013.01); *B65D 83/14* (2013.01); *Y10T 29/49826* (2015.01)

(56) References Cited

U.S. PATENT DOCUMENTS

| | | |
|---|---|---|
| 2003/0178507 A1 | 9/2003 | Maria Rijn Van |
| 2004/0179073 A1 | 9/2004 | Valley et al. |
| 2006/0213408 A1* | 9/2006 | Christ ..................... B05B 1/14 111/200 |
| 2007/0176990 A1 | 8/2007 | Urayama et al. |
| 2009/0013993 A1* | 1/2009 | Bird et al. ............... 128/200.15 |

* cited by examiner

PRIOR ART

ATOMISING BODY, ATOMISING DEVICE, INHALER, MANUFACTURING METHOD OF MANUFACTURING AN ATOMISING BODY AND ASSEMBLY METHOD FOR ASSEMBLING AN ATOMISING DEVICE

CROSS-REFERENCE TO RELATED APPLICATIONS

This application is the National Stage of International Application No. PCT/NL2010/000070, filed Apr. 22, 2010, which claims the benefit of Netherlands Application No. 2002787, filed Apr. 23, 2009, the contents of which is incorporated by reference herein.

FIELD OF THE INVENTION

The present invention relates to an atomising device comprising an atomising body.

BACKGROUND OF THE INVENTION

Atomising bodies and atomising devices are e.g. known from WO 02/18058.

The atomising bodies and devices as known in the art e.g. comprise a first membrane and a second membrane mounted to a support element comprising a fluid conduit (e.g. a cavity) arranged to guide a fluid from the first membrane to the second. In the embodiments as disclosed in the art, the support element has a cavity extending from a first surface of the support element to a second surface of the support element. The membranes are mounted to the respective first and second surfaces thereby covering the cavity. In the embodiments as described, the first membrane operates as a nozzle to atomise a fluid from the cavity whereas the second membrane operates as a sieve to filter a fluid that is received in the cavity through the second membrane. The cavity arranged between the membranes can e.g. be obtained by mounting the membranes (e.g. micro-machined structures) to a support element containing the cavity. Such an element having a hole through it can be covered at both sides by a membrane. In order to manufacture an atomising body in such way, a minimal strength of the membranes is required to mount them to the element. Further, means have to be provided for the membranes to adhere to the element. The membranes can e.g. be glued to the element. The application of a glue may however be unwanted for some applications, e.g. medical applications. The minimal strength imposed upon the membranes in order to mount them to the element poses a limitation to the miniaturisation of the atomising head. It is further suggested in WO 02/18058 to provide the membranes to a solid support element and etch a cavity between the membranes through the pores of the membranes. Such an approach however may be cumbersome as the etching process through the available pores may take a long time.

In view of the above, it is an object of the present invention, to provide an alternative way of manufacturing an atomising body for use in an atomising device.

SUMMARY OF THE INVENTION

According to an aspect of the invention, there is provided a method of manufacturing an atomising body, the method comprising the steps of

- providing a support element having a first layer on a first surface of the support element and a second layer on a second surface of the support element, the first layer comprising a first perforated membrane and the second layer comprising a process orifice and a second perforated membrane arranged adjacent the process orifice,
- etching a cavity through the support element, forming a fluid connection from the process orifice to the first perforated membrane and from the first perforated membrane to the second perforated membrane, by providing an etching substance to the process orifice.

The method of manufacturing an atomising body according to the invention utilizes a support element which is provided with a first and second perforated membrane and a process orifice.

In accordance with the present invention, a perforated membrane is used to allow a fluid to enter the cavity of the atomising body or leave the atomising body. Applied in an atomising body according to the invention, a perforated membrane can e.g. be obtained by providing a layer on a support element and applying perforations to the layer. The required pattern of the perforation or perforations can be provided by a lithographic process. As an example, a membrane can be made from a silicon nitride layer. When the required pattern of perforations such as pores is provided (e.g. by a lithographic process), the perforation or perforations can be realised in the silicon nitride layer by e.g. an etching process. In an embodiment, the first membrane of the atomising body operates, in use, as a nozzle.

The second layer of the support element is provided with a process orifice and a second perforated membrane arranged adjacent the process orifice on a second layer used to etch a cavity in the support element. Within the meaning of the present invention, a process orifice is understood as a comparatively large perforation or perforations in the second layer, large compared to the size of the perforations of the first membrane or the perforations of the second membrane. By applying a comparatively large perforation, the etching process (e.g. a wet etching process using KOH or a reactive ion etching process using e.g. $SF_6$ gas) of providing a cavity extending between the first and second layer of the support element is facilitated. It is acknowledged that etching processes are known in general. In order to generate a cavity between two layers of a support element by etching, the material between the two layers needs to be accessed by an etching substance. Within the meaning of the present invention, etching substance is used to designate a material or substance that can be applied to perform an etching process. Examples of such etching substance are KOH or tetramethylammonium hydroxide (TMAH). The etching substance can also comprise a plasma for etching the cavity. Examples of such a plasma are $SF_6$ or $CHF_3$. It has been devised that accessing the support element through the perforations of a membrane can be cumbersome and may not result in the required cavity (i.e. a cavity forming a fluid connection from the first layer to the second layer) being realised. Phrased differently, the pores as provided in a membrane may be insufficient to enable the required etching process. In practice, the etching process can come to a stop prior to the completion of the cavity.

The process orifice enables the etching substance to access the support element. This way the etching process does not have to rely on the etching substance entering the support element via the perforations of the first membrane or the second membrane. As a result of the etching process, a cavity forming a fluid connection from the process orifice to the first perforated membrane and from the first perforated membrane to the second perforated membrane is established. Such a cavity enables, during use of the atomising body as obtained by the manufacturing method, a fluid to enter the cavity through the process orifice and leave the cavity through the first perforated membrane.

In order to manufacture the process orifice or the membranes that e.g. operate as a nozzle or a sieve, etching processes such as isotropic and anisotropic etching can be applied.

In case the first perforated membrane is to be applied as a nozzle, a fluid entering the cavity of the atomising body through the process orifice can e.g. be filtered by providing a cover covering the process orifice, the cover e.g. being made or comprising a porous material. The second perforated membrane of the atomising body can e.g. operate as a sieve.

The manufacturing method according to the invention thus provides a process orifice that facilitates accessing a volume of the support element arranged between the membranes. As such, the process orifice is arranged adjacent to the second perforated membrane. By providing the process orifice, an access is generated that enables an etchant to remove part of the support element that is located between the first and second membrane.

In accordance with the present invention, a cavity extending from a first perforated membrane to a second perforated membrane is provided by etching the support element to enable a fluid flow between the first and second membrane. By doing so, no manipulation of the membranes (i.e. the mounting of the membranes to a supporting structure) is required to obtain a cavity enclosed by two membranes. As a consequence, the strength requirements for the membranes can be less stringent thus allowing the application of very thin membranes (0.5 to 5 µm thick). The application of these thin membranes may result in a reduced pressure drop over the membranes thus allowing a lower operating pressure to be applied.

Atomising bodies as obtained by the manufacturing method according to the invention may advantageously be applied in an atomising device. As such according to an aspect of the invention, there is provided an atomising body comprising
  a support element having a first layer on a first surface of the support element and a second layer on a second surface of the support element, the first layer comprising a first perforated membrane and the second layer comprising a process orifice,
  a cavity through the support element, the cavity forming a fluid connection from the process orifice to the first perforated membrane.

Within the meaning of the present invention, the process orifice of the atomising body according to the invention is understood as a comparatively large perforation or perforations, large compared to the size of the perforations of the first membrane. As an example, the perforations of the first membrane may have a size (e.g. a diameter) varying from 0.5 to 10 micron whereas the process orifice can comprise one or more perforations having a size >10 µm in diameter. The size of the process orifice enables the transport of etching substance into the atomizing body and/or the transport of reactants out of the atomizing body.

In an embodiment, the atomising body further comprises a cover for covering the process orifice. Such a cover can e.g. be made from a porous material and, in use, operate as a sieve, prohibiting particles to enter the cavity through the process orifice.

In a preferred embodiment, the cross-section of the process orifice is smaller than an area covering the first perforated membrane. This may e.g. provide the advantage of enabling the etching process without increasing the overall size of the atomising body. It may also minimize the 'dead volume' of liquid inside the atomizing body, which enables priming out air bubbles. Selecting the appropriate size for the process orifice can thus be considered a trade-off between selecting the process orifice sufficiently large to enable the etching of the cavity and sufficiently small to keep the overall size of the atomising body as small as possible.

According to a further aspect, of the invention, there is provided an atomising device comprising an atomising body and a supporting structure, the atomising body comprising:
  a support element having a first layer on a first surface of the support element and a second layer on a second surface of the support element, the first layer comprising a first perforated membrane and the second layer comprising a second perforated membrane,
  a process orifice arranged on at least one of the first or second layer, the orifice being arranged adjacent the first or second perforated membrane,
  a cavity forming a fluid connection from the first perforated membrane to the second perforated membrane,
  and wherein the atomising body is attached to a surface of the supporting structure, thereby substantially covering the process orifice.

An atomising device according to the invention comprises a supporting structure and an atomising body. The supporting structure can e.g. comprise an inlet for receiving a fluid and providing the fluid, e.g. under pressure, to the atomising body. In use, the fluid received can e.g. enter the atomising body through the second membrane e.g. a sieve. The second membrane may thus operate as a filter to prohibit particles, that may block the downstream first perforated membrane, to enter the cavity of the atomising body. The fluid received in the cavity can leave the atomising body through the first membrane which can e.g. comprise a nozzle orifice thereby forming a vapour or a mist. Within the present application, terms such as vapour, spray, aerosol or mist are deemed to be equivalent as are terms as atomising, vaporising, spraying and nebulising. The second perforated membrane may also act as a microbial filter, to prevent microbes to pass through the atomising body upstream towards a fluid container. The second membrane may block microbes when the perforations are smaller than 2 micron, preferably smaller than 1 micron, preferably smaller than 0.5 micron, preferably smaller than 0.25 micron.

The supporting structure of the atomising device according to the invention further comprises a surface for covering the process orifice of the atomising body. By covering the process orifice, fluid is substantially prohibited from entering or leaving the atomising body without passing through the filter membranes of the atomising body.

The supporting structure of the atomising device can e.g. have a tubular shape.

The assembly or mounting of an atomising body in an atomising device such that a process orifice of the atomising body is substantially closed or covered can be realised in various ways. Therefore, according to a further aspect of the invention, there is provided a manufacturing method for an atomising device, the method comprising the steps of
  providing an atomising body as obtained from the manufacturing method according to the invention,
  mounting the atomising body to a surface of a supporting structure, thereby substantially covering the process orifice of the atomising body,
  attaching the atomising body to the supporting structure.

Attaching the atomising body to the supporting structure can e.g. be done by applying a glue to the surface of the supporting structure or by bonding.

In a preferred embodiment, the supporting structure is made from a thermoplastic and the attaching of the atomising body to the structure is realised by heating the atomising body in order to adhere the atomising body to the structure at least at the surface. By heating the atomising body, parts of the supporting structure that are in heat exchanging contact with the atomising body will melt and may, as a result thereof adhere to the atomising body.

Attaching the atomising body to the supporting structure in this manner does not require the use of additional components or materials such as glue. Avoiding such components or materials can facilitate the acceptance of the atomising device for pharmaceutical or medical applications because, for these applications, each material that may come in contact with a drug substance or patient needs to be safe, tested and certified.

The atomising body or atomising device according to the invention may e.g. be powered by a manual spray pump or a spring driven pump mechanism. The fluid can also be powered by a pressurised container, either with a continuous valve or a metered valve. Such inhalers can e.g. combine an atomising body, operating as a spray nozzle, a valve that can be actuated by a user and a pressurised container for providing a fluid to the atomising body. The valve can e.g. be a continuous valve or a metered valve. Therefore, according to an aspect of the invention, there is provided an inhaler comprising
- a container for containing a pressurised gas and a fluid,
- an atomising device according to the invention and
- a valve for enabling the fluid to flow from the container to the atomising device, wherein an atomising body of the atomising device in use operates as a nozzle for spraying the fluid.

In an embodiment of the present invention, an inhaler is provided comprising:
- a container for containing a fluid,
- an atomising device according to the invention and
- a passage enabling the fluid to flow from the container to the atomising device, wherein an atomising body of the atomising device in use operates as a nozzle for spraying the fluid and wherein, in use, a user action upon the container enables a volume of the container containing the fluid to be reduced, thereby providing a dose of fluid to the user.

In the embodiment, the volume reduction can e.g. substantially continuous and directly affects the amount of fluid (i.e. the dose) that is administered. In such an inhaler, the dose administered thus depends on the user action on the container. As such, only the total dose as available in the container is fixed, whereas the different doses that are applied sequentially in order to empty the container, can be adjusted/selected by the user by appropriate action on the container. In an embodiment, the container can comprise a syringe or syringe-like device for containing the fluid.

Various embodiments covering the different aspects of the present invention are described below with reference to the following drawings wherein corresponding reference numbers indicate corresponding parts or elements.

DETAILED DESCRIPTION OF THE INVENTION

Figure 1A:
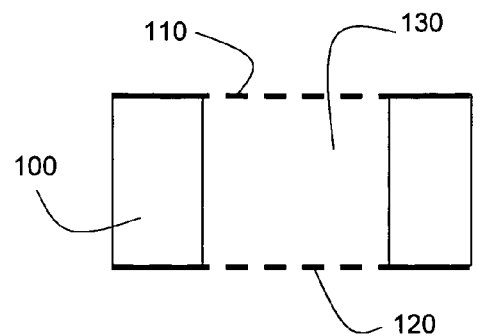
FIGS. 1a-1b schematically depict atomising bodies as known in the art.
Figure 1B:
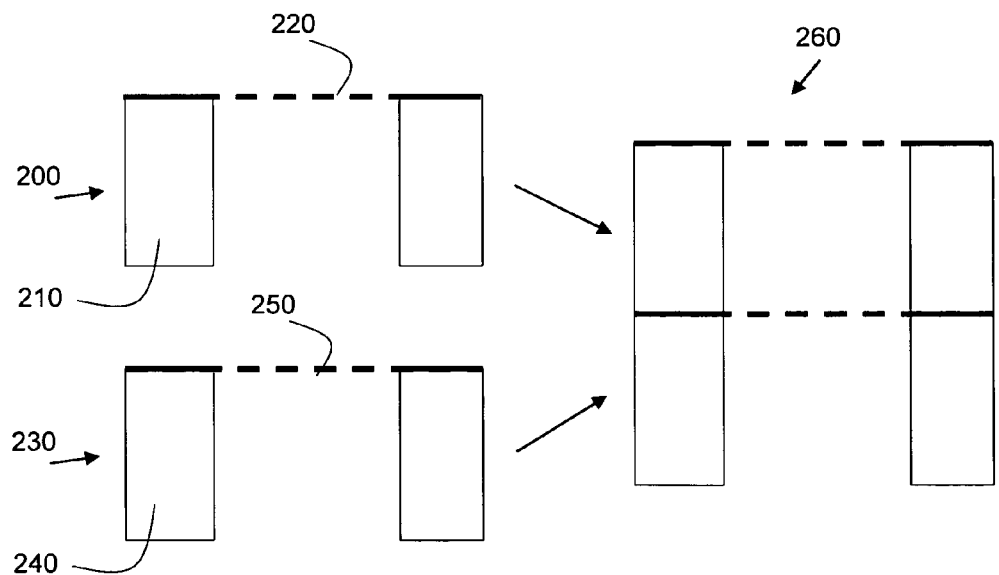

FIG. 1a schematically depicts a known atomising body as disclosed in WO 02/18058. WO 02/18058 discloses atomising bodies comprising a support element 100, a nozzle plate 110 and a filtration plate 120 as indicated in FIG. 1a. The support element comprises a cavity 130 extending from the nozzle plate 110 to the filtration plate thereby providing a fluid connection between both plates. WO 02/18058 discloses embodiments of an atomising body wherein the atomising body is obtained by assembling (e.g. by gluing) a first element 200 comprising a support element 210 and a nozzle plate 220 to a second element 230 comprising a support element 240 and a filtration plate 250 resulting in an atomising body 260. In order to obtain the atomising body 260, it thus requires the assembly of first and second elements 200 and 230. Such an assembly may require accurate tooling and may thus be rather expensive. Furthermore, it may result in particle contamination during the assembly. In order to avoid this, it has been suggested to realise the cavity between the nozzle plate and filtration plate by applying an etching process through the pores through the plates. It has been observed by the inventors that such etching may take a long time or may not result in a cavity extending between the membranes at all, depending on the geometry of the support element and/or membranes. The present invention therefore provides an improved manufacturing method for an atomising body.

FIGS. 2a-2f schematically depict different processing steps of an embodiment of the manufacturing method to obtain an atomising body according to the invention. The manufacturing method as illustrated can utilize a structure 300 comprising a support element 310 having a first layer 320 on a first surface 330 of the support element and a second layer 340 on a second surface 350 of the support element, the first layer comprising a first perforated membrane 360 and the second layer comprising a second perforated membrane 370. Such a structure can e.g. be obtained by the following process:
   utilizing a support element such as silicon, the silicon is covered on two surfaces with a layer of silicon nitride to obtain the layers 320 and 340,
   using an etching process such as reactive ion etching (RIE), pores can be etched in the layers, thereby forming membranes.

The first and second membranes are perforated structures that are intended for use as a nozzle and a sieve or filter respectively once the atomising body is manufactured. The first membrane, to be used as a nozzle may, as an example, be provided with one or more protrusions or orifices, e.g. having a diameter of 0.5 to 10 micron. The orifices may e.g. have a substantially circular shape or may e.g. have a rectangular slit-shape. In an embodiment, the nozzle comprises an array of approx. 300 orifices or pores. The second membrane, to be used as a filter or sieve, can e.g. comprise an array of pores, typically approx. 10000 pores of 0.2 to 5 micron in size.

Figure 2A:
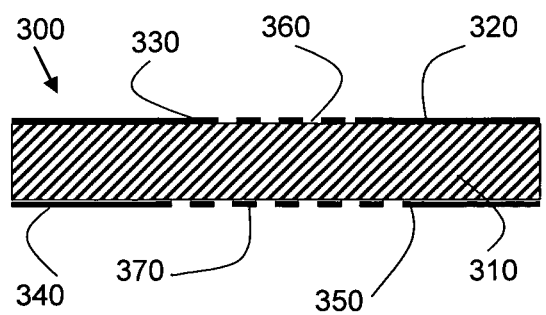
FIGS. 2a-2f schematically illustrated an embodiment of the manufacturing process of an atomising body according to the present invention.
Figure 2B:
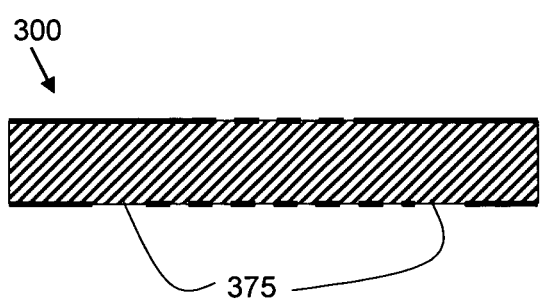

According to the embodiment of the manufacturing method of the invention, a process orifice is further provided on at least one of the first or second layer, the orifice being arranged adjacent the first or second membrane. FIG. 2b schematically depicts a structure 300 similar to the structure shown in FIG. 2a apart from the occurrence of two process orifices 375 arranged adjacent the second membrane. As the process orifices are not intended to be used as either a nozzle or as part of the filter or sieve, there are less restrictions with respect to the size of the orifice. The orifices can e.g. be made 10 or 50 times larger than the pores in the sieve or the pores in the nozzle. The process orifice or orifices can be obtained with a similar or with the same etching process as used to provide the first and second membrane orifices. It will be appreciated by the skilled person that the process orifice or orifices can be manufactured together with the membrane orifices (i.e. in one processing step) or in two consecutive steps. With respect to the position and size of the process orifices, various options exist: A single process orifice can be provided adjacent either the first or second membrane. Alternatively, multiple process orifices can be provided either adjacent one of the membrane or adjacent both membranes. In a preferred embodiment, two process orifices are provided, as indicated in FIG. 2b on opposite sides of either the first or second membrane.

Figure 2C:
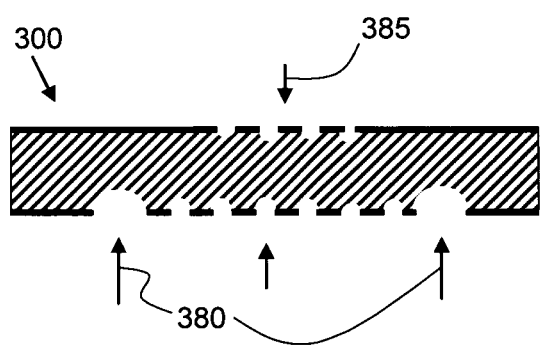
Figure 2D:
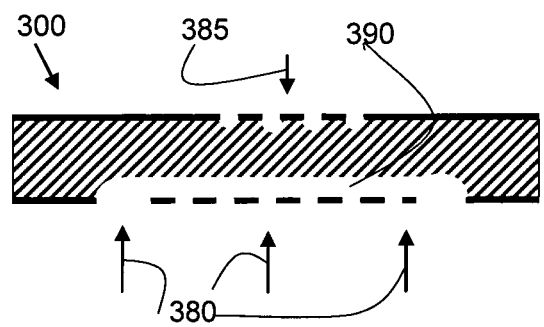
Figure 2E:
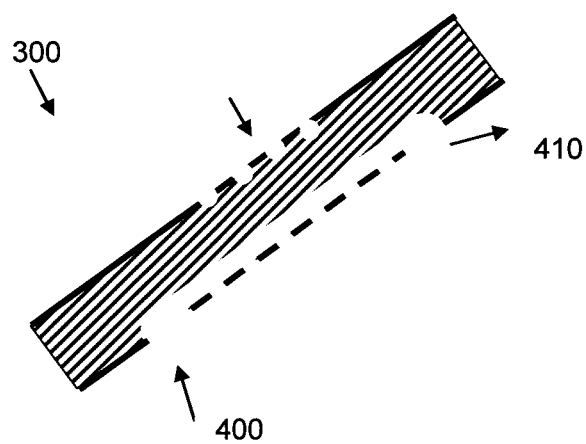
Figure 2F:
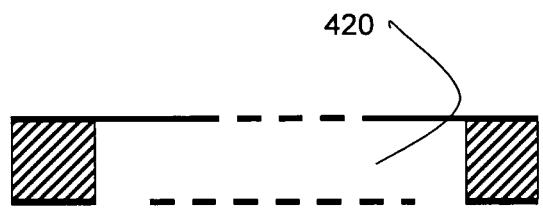

In order to etch a cavity extending between the two membranes, an etching substance is applied to the process orifices, as indicated by the arrows 380 in FIG. 2c. As shown in FIG. 2c, the etchant may also be applied to the membrane(s) (as e.g. indicated by the arrow 385), this is however not a requirement for the manufacturing method according to the invention. The structure 300 can e.g. be immersed entirely in an etchant thus etching the support element through the first perforated membrane, the second perforated membrane and the process orifice(s). When the perforations in the membranes are comparatively small and/or the distance between the two membranes is comparatively large, the effect of applying an etching substance to the membranes may however be limited and not result in a cavity forming a fluid connection from the first perforated membrane to the second perforated membrane. By applying an etching substance to the process orifice however, such a cavity can be established. As an etching substance, potassium hydroxide (KOH) can be applied. Other examples of suitable etching substances include TMAH and ethylenediamine pyrocatechol (EDP). Applying the etching substance to the process orifices and optionally to the membranes can result in a passage 390 connecting both process orifices as indicated in FIG. 2d. In order to realise a cavity extending between the membranes (i.e. forming a fluid connection from the first perforated membrane to the second perforated membrane), it may be advantageous to tilt the structure 300, the structure e.g. being immersed in an etching liquid, as shown in FIG. 2e. By doing so, reactants of the etching process, such as H2 gas are facilitated to leave the structure through the second orifice via the passage, as indicated by the arrow 410. As a result, fresh etching substance is pulled inward through the lowest process orifice as indicated by the arrow 400; the passage 390 thus operating as a kind of pump refreshing etching fluid inside the passage 390. As a result of the etching process, cavity 420 as indicated in FIG. 2f can thus be obtained. The cavity 420 extends from the first membrane to the second membrane thereby enabling a fluid communication between both membranes.

Figure 3:
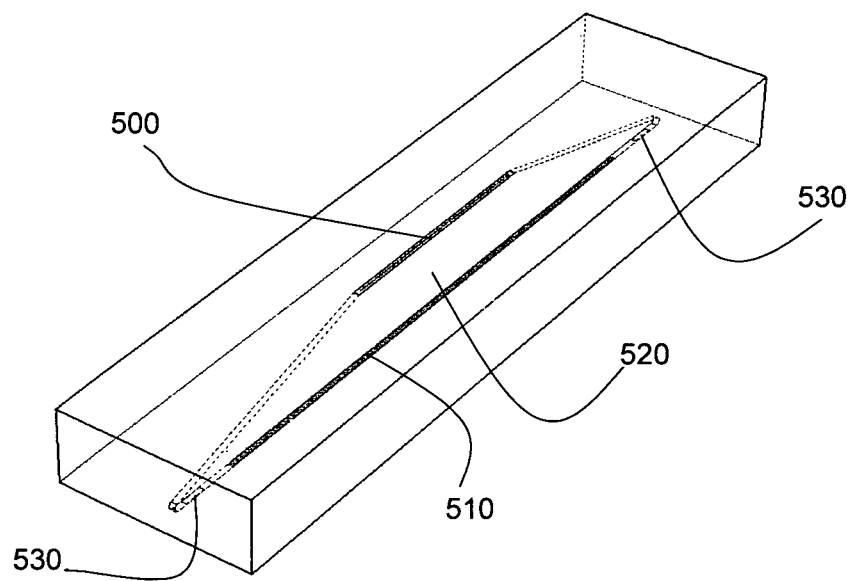
FIG. 3 schematically depicts a 3D view of an atomising body as obtained by a manufacturing method according to the invention.

FIG. 3 schematically depicts a 3D view of an atomising body as obtained by the manufacturing method according to the invention. The 3D view schematically shows the first and second membranes 500, 510 and the cavity 520 etched between them. On opposite sides of the membrane 510, process orifices 530 are provided that are used for etching the cavity 520 between the membranes.

Figure 4A:
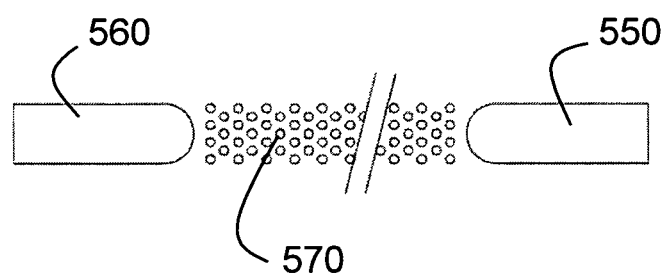
FIG. 4a schematically depicts a top view of a filter membrane and two process orifices arranged on opposite sides of the membrane.

FIG. 4a schematically depicts a top view of a possible configuration of two process orifices 550, 560 and a membrane 570 arranged between them. In the configuration as shown, the membrane is a two-dimensional array of substantially circular pores.

The manufacturing method as illustrated above employs two process orifices arranged on opposing sides of one of the membranes. It should be emphasised that other arrangements are possible as well and provide similar benefits in facilitating the etching process. Examples of such arrangements are:
   use of a single process orifice adjacent one of the membranes,
   use of a single process orifice arranged substantially in the centre of one of the membranes,
   use of a process orifice adjacent each of the membranes,
   use of an alternating array of process orifices and perforated membranes, etc.

Figure 4B:
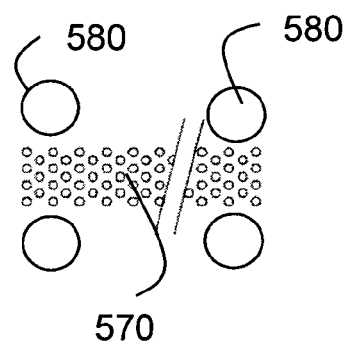
FIG. 4b schematically depicts another top view of a filter membrane and four process orifices arranged adjacent the membrane.

As an example, FIG. 4b schematically depicts a top view of four process orifices 580 arranged along two opposing sides of a membrane 570.

Figure 5A:
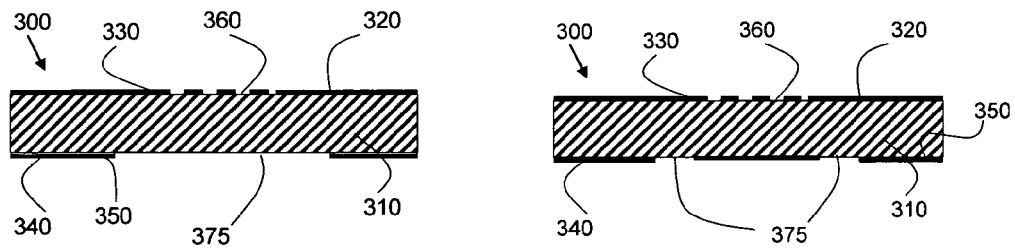
FIGS. 5a-5c schematically illustrate another embodiment of the manufacturing process of an atomising body according to the present invention.
Figure 5B:
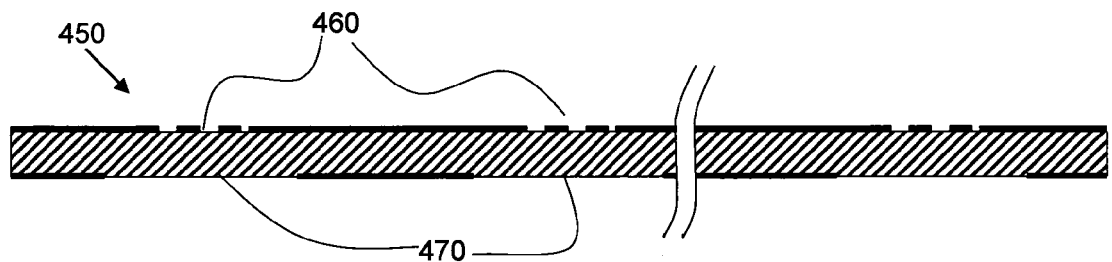
Figure 5C:
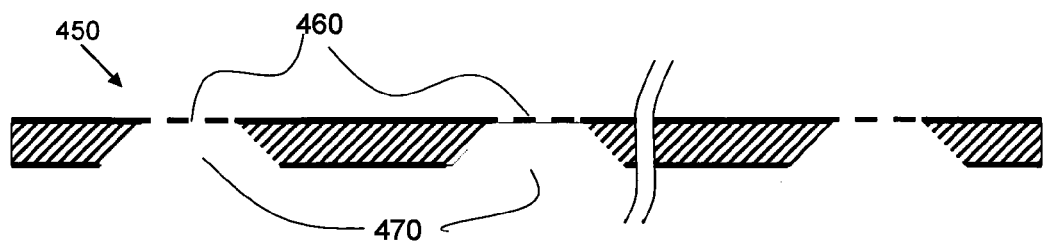

Rather than utilizing from a structure 300 comprising a support element 310 having a first layer 320 on a first surface 330 of the support element and a second layer 340 wherein the first layer comprises a first perforated membrane 360 and the second layer comprising a second perforated membrane, the manufacturing method according to the invention may equally utilize a structure 300 comprising a support element 310 having a first layer 320 on a first surface 330 of the support element and a second layer 340 on a second surface 350 of the support element wherein the first layer comprises a first perforated membrane 360 and the second layer comprising a process orifice 375. Two possible arrangements are schematically depicted in FIG. 5a. On the left is an arrangement with a single process orifice 375, the arrangement on the right comprises a pair of orifices 375. Such a structure can be etched in a similar manner as described above. In practice, multiple atomising bodies can be manufactured substantially at the same time by providing an array of membranes 460 and process orifices 470 on two surfaces of a support element, such a structure 450 schematically being shown in FIG. 5b. When the etching process as described in FIGS. 2c to 2e is applied, the structure 450 obtained can be as shown in FIG. 5c having cavities between the first membranes 460 and the process orifices 470. It is further worth noting that a surface of the cavity as obtained by the etching process should not be limited to the surface described by the process orifice. Preferably, the surface of the cavity on the layer comprising the process orifice is larger than the surface of the surface of the process orifice.

As already mentioned above, it may be advised to provide a sieve or filter to filter a fluid that enters the cavity. In the embodiments utilizing a support element having a second membrane, the second membrane can e.g. be used to filter the fluid. With respect to the embodiment as shown in FIG. 5c, filtering can e.g. be obtained by providing a cover to the process orifice, the cover comprising a filter or sieve. In an embodiment, such a filter or sieve can be manufactured from a porous material.

Figure 6:
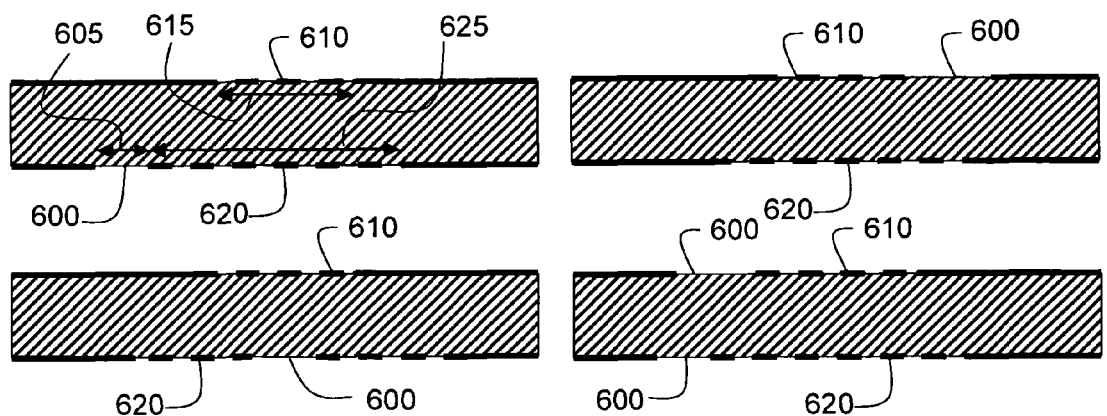
FIG. 6 schematically depicts different arrangements of process orifices as can be applied in the manufacturing method and atomising body according to the invention.

FIG. 6 schematically depicts some of the possible arrangements. In the cross-sectional views reference numbers 600, 610 and 620 are used to indicate the process orifices, the first membrane and the second membrane respectively. In a preferred embodiment, the atomising body according to the invention comprises a process orifice 600 having a cross-section (e.g. indicated by the arrow 605) that is smaller than the area covered by the first or second perforated membrane (indicated by the arrows 615 resp. 625). In case the atomising body comprises a second perforated membrane (e.g. in use operating as a sieve or as a microbial protection), the process orifice may not be required during normal operation of the atomising body to allow a fluid to enter or leave the cavity. Therefore, it may be advantageous to select the cross-section of the process orifice smaller than the area covered by the first or second perforated. This may minimize the 'dead volume' inside the atomising body, which is advantageous for priming out air bubbles. It may also improve the start and stop behaviour of the spray.

Figure 7:
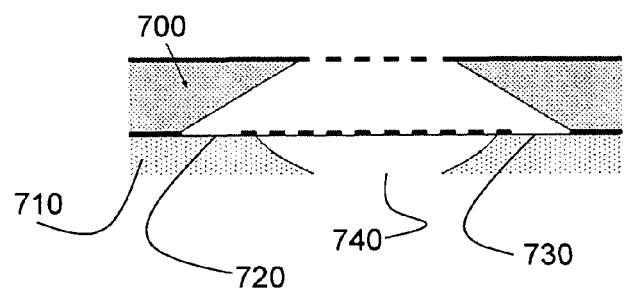
FIG. 7 schematically depicts an atomising body according to the invention provided with a cover.

In order to be applied in an atomising device, the atomising body can be provided with a cover covering the process orifice or orifices. FIG. 7 schematically depicts such an arrangement. The atomising body 700 as shown is provided with a cover 710 arranged to cover the process orifices 720 and 730 of the atomising body. The cover 700 further comprises an opening 740 for receiving a fluid. The cover can, as an example, be manufactured from glass, ceramics, silicon, metal or plastic or a combination thereof. The cover can also be made from or comprise a porous material, ensuring that no particles enter the cavity through the process orifice or orifices. In case a porous material is used to cover the process orifice or orifices, the material may also cover part or all of the membrane operating as a sieve. In this embodiment, the porous material operates as a sieve or filter too.

In order to assemble the cover to the atomising body, various methods can be applied. As an example, the atomising body and cover can be assembled using 'direct bonding'. The direct bonding occurs when two clean and smooth surfaces are brought closely together, and are held together by the so-called Van Der Waal's forces. The bonding can be stimulated or improved by adding heat and/or electricity. The latter process also being known as anodic bonding.

As an alternative, the cover can be glued to the atomising body. It can however be noted that, for pharmaceutical or medical applications, the bonding methods are preferred as they avoid the use of glue.

Another method that avoids the use of glue but which does not rely on direct bonding is the application of a thermoplastic as a cover material. The thermoplastic cover can be rigidly mounted to the atomising body by heating the atomising body or parts of the body close to the plastic cover. By heating the atomising body, part of the plastic cover close to the atomising body can (partly) melt and thus become a melted fluid plastic. The melted plastic may flow and substantially close the process orifice or orifices. When subsequently, the plastic cools down, it will become solid again. Shrinkage of the plastic may cause a secure seal.

The method of closing the process orifices by melting and subsequently solidifying a plastic part may have the advantage over the direct bonding methods that no close direct contact is required between the atomising body and the cover. As the membranes of the atomising body are fragile structures, in particular after the creation of the cavity between the membranes, bringing a cover in close contact to the membrane in order to realise a direct bonding, may result in damaging the membrane. As a result, the membrane's function as a nozzle or sieve can be compromised.

Once a cover is provided, the atomising body including the cover can be mounted to a supporting structure thereby forming an atomising device.

Figure 8:
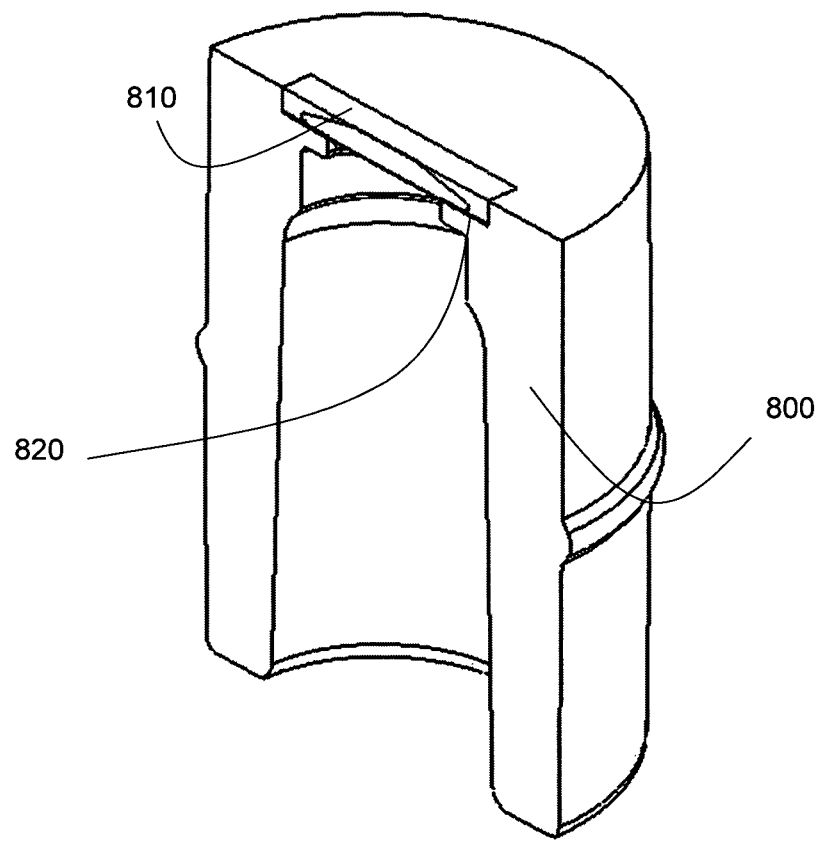
FIG. 8 schematically depicts a cross-sectional view of part of an atomising device according to the invention.
Figure 9A:
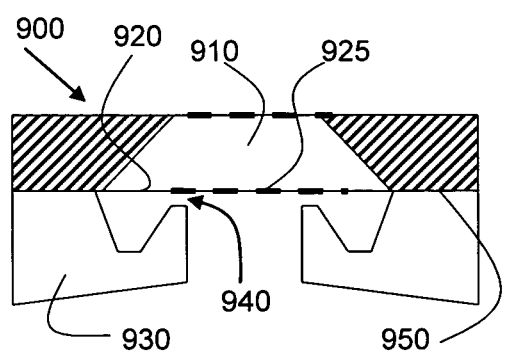
FIGS. 9a-9b schematically depict cross-sectional views of part of other atomising devices according to the invention.
Figure 9B:
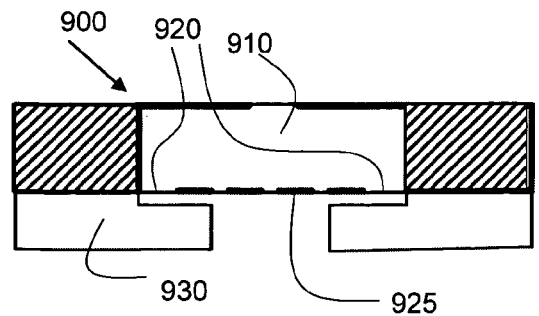

Instead of providing a cover to an atomising body in order to substantially close a process orifice of the atomising body, the process orifice of the atomising body can be sealed off during the assembly of the atomising device. In order to realise this, an atomising device is manufactured by assembling a supporting structure having a surface and an atomising body and whereby the surface of the supporting structure is shaped in such manner that when the atomising body is mounted to it, the process orifice is substantially closed off. By doing so, the step of separately mounting a cover to the atomising body, as explained above, is no longer required. A further advantage of covering the process orifice by a surface of the supporting structure of the atomising device is that it reduces the number of components required to assemble an atomising device according to the invention. FIG. 8 schematically depicts an atomising device comprising a supporting structure 800 and an atomising body 810. The supporting structure comprises a surface 820 arranged to receive the atomising body 810. With respect to the sealing (or closing off) of the process orifices, it is worth nothing that the orifices need not be closed off entirely. In order to avoid particles to enter or leave the cavity, it may be sufficient to ensure that the opening towards the process orifice is small enough to filter particles. In order to illustrate this, FIG. 9a schematically depicts an atomising body 900 according to the invention, the atomising body comprising a cavity 910 and a process orifice 920 adjacent a membrane 925. The process orifice is substantially covered by a cover 930. The cover 930 does not entirely cover the process orifice, a small gap 940 remains between the cover 930 and the layer 950 comprising the membrane and orifice. By appropriate scaling of cover and gap 940, one can obtain that substantially all the fluid enters the cavity through the membrane 925. FIG. 9b schematically depicts an alternative embodiment of an atomising body 900 according to the invention including a cover 930 which does not entirely cover the process orifice 920 arranged adjacent a perforated membrane 925. Also in this embodiment, by appropriate scaling of cover and gap between the cover and the process orifice 920, one can obtain that substantially all the fluid enters the cavity 910 through the membrane 925.

Figure 10:
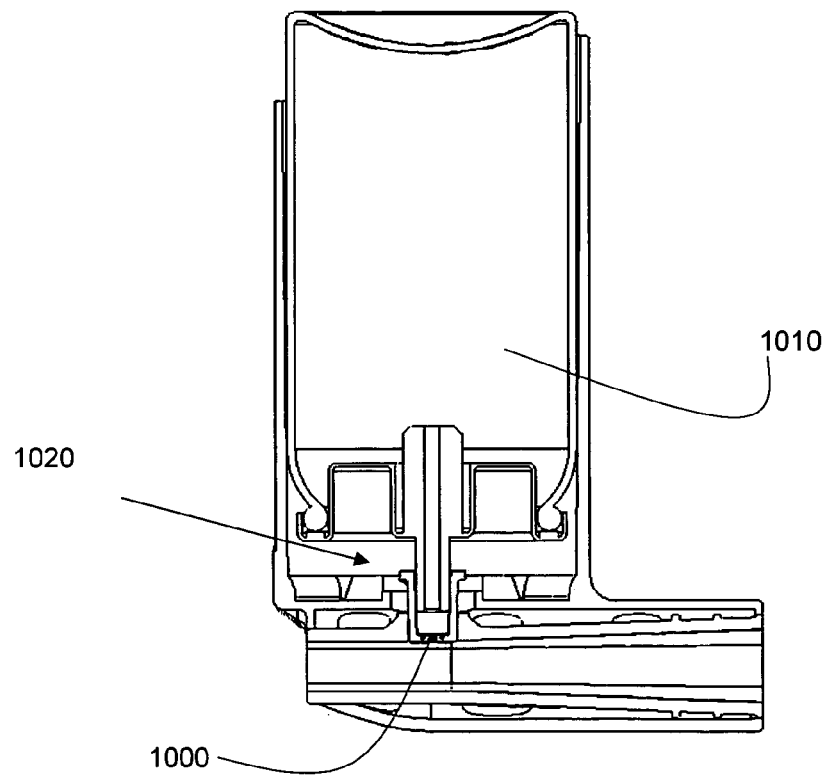
FIG. 10 schematically depicts a cross-sectional view of an inhaler according to the invention.

The atomising device according to the invention may, as an example, be applied in an inhaler as schematically depicted in FIG. 10. Such an inhaler comprises an atomising device having an atomising body 1000, and a container 1010 which, in use, can be provided with a fluid and a pressurised gas. The inhaler further comprises a valve 1020 for enabling the fluid to flow from the container 1010 to the atomising device. The atomising body 1000 of the atomising device may then, in use, operate as a nozzle for spraying the fluid. The valve as applied can e.g. be a continuous valve enabling the application of a variable dose or a metered valve resulting in substantially the same dose being administered each time the valve is operated.

Figure 11:
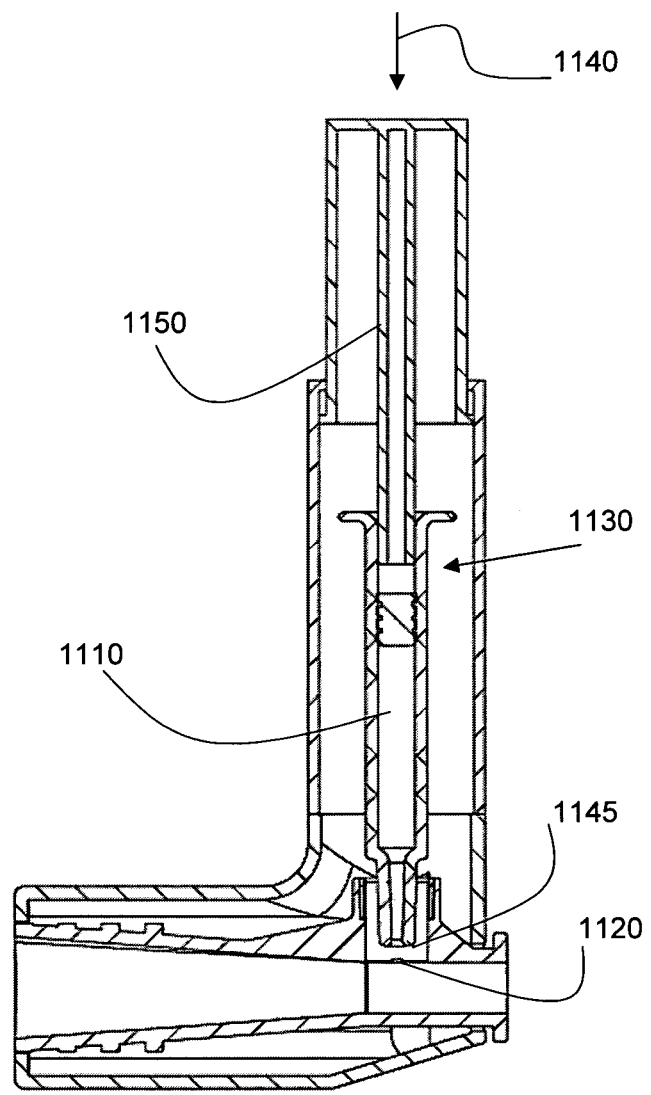
FIG. 11 schematically depicts a cross-sectional view of another inhaler according to the invention.

In FIG. 11, another embodiment of an inhaler according to the invention is schematically shown. Similar to the inhaler shown in FIG. 10, the inhaler comprises a container 1110 for in use containing the substance to be administered and an atomising device according to the invention comprising an atomising body 1120. As can be seen, the container as applied in the inhaler comprises a syringe or syringe-like device 1130 for containing the substance. When a user applies a force (indicated by the arrow 1140) to the plunger 1150 of the syringe, the volume of the container comprising the fluid or substance is reduced thereby forcing part of the fluid or substance to leave the inhaler via a passage 1145 to the atomising body 1120 which operates as a nozzle for spraying the fluid or substance. When a user presses down the plunger during an inhalation, a variable dose is released, depending on the force exerted on the plunger. As such, the user may determine the rate at which the total volume of the syringe is emptied.

Exemplary embodiments of the present invention have been described above. It should be noted that the embodiments are merely intended to illustrate the invention, the scope of the invention only being limited by the following claims.

The invention claimed is:

1. A method of manufacturing an atomising body for an atomising device, the method comprising the steps of
   providing a support element having a first layer on a first surface of the support element and a second layer on a second surface of the support element, the first layer comprising a first perforated membrane and the second layer comprising a process orifice and a second perforated membrane arranged adjacent the process orifice; and
   etching a cavity through the support element, the cavity forming a fluid connection from the process orifice to the first perforated membrane and from the first perforated membrane to the second perforated membrane, by providing an etching substance to the process orifice;
   juxtaposingly disposing a cover at the second perforated membrane and over the process orifice; and
   sealing the process orifice by the cover to form the atomising body,
   wherein the step of sealing the process orifice by the cover comprises:
   covering the process orifice by the cover while maintaining a small gap between the cover and the process orifice, the gap configured to be small enough to filter particles so as to prevent particles from entering the cavity via the process orifice.

2. The method according to claim 1 wherein a cross-section of the process orifice is substantially larger than a cross-section of perforations of the second perforated membrane.

3. The method according to claim 2 wherein the first perforated membrane comprises a one-dimensional or two-dimensional array of nozzle orifices.

4. The method according to claim 3 wherein a cross-section of the process orifice is substantially larger than a cross-section of a nozzle orifice of the first perforated membrane.

5. The method according to claim 2 wherein the second perforated membrane comprises a one-dimensional or two-dimensional array of sieve pores.

6. The method according to claim 5 wherein a cross-section of the process orifice is substantially larger than a cross-section of a sieve pore of the second perforated membrane.

7. The method according to claim 2 wherein the process orifice comprises a pair of orifices, each process orifice of the pair of orifices arranged on opposite sides, respectively, of the first or second perforated membrane.

8. The method according to claim 1 wherein the support element comprises silicon and the first and second layer comprise silicon nitride.

9. The method according to claim 1, wherein when the small gap is maintained between the cover and the process orifice, the cover is made from glass, ceramics, silicon, metal or plastic or is made from a porous material.

10. An atomising body comprising
    a support element having a first layer on a first surface of the support element and a second layer on a second surface of the support element, the first layer comprising a first perforated membrane and the second layer comprising a process orifice and a second perforated membrane arranged adjacent the process orifice;
    a cavity through the support element, the cavity forming a fluid connection from the process orifice to the first perforated membrane and from the first perforated membrane to the second perforated membrane;
    a cover juxtaposingly disposed at the second perforated membrane and over the process orifice for covering the process orifice,
    wherein a small gap is provided between the cover and the process orifice, the gap configured to be small enough to filter particles so as to prevent particles from entering the cavity via the process orifice.

11. The atomising body according to claim 10 wherein the second perforated membrane comprises perforations that are smaller than 2 micron for, in use, operating as a bacterial filter.

12. The atomising body according to claim 10 wherein the cover is made from glass, ceramics, silicon, metal or plastic.

13. The atomising body according to claim 10 wherein the cover is made from a porous material.

14. The atomising body according to claim 10 wherein the cover further covers part or all of the second perforated membrane.

15. The atomising body according to claim 10 wherein a cross-section of the process orifice is substantially larger than a cross-section of a perforation of the second perforated membrane.

16. An atomising device comprising:
    a support element having a first layer on a first surface of the support element and a second layer on a second surface of the support element, the first layer comprising a first perforated membrane and the second layer comprising a process orifice and a second perforated membrane arranged adjacent the process orifice;
    a cavity etched through the support element, the cavity forming a fluid connection from the process orifice to the first perforated membrane and from the first perforated membrane to the second perforated membrane; and a supporting structure having a surface juxtaposingly disposed at the second perforated membrane and over the process orifice;

wherein a small gap is provided between the surface of the supporting structure and the process orifice, the gap configured to be small enough to filter particles so as to prevent particles from entering the cavity via the process orifice; and wherein the surface of the supporting structure is arranged substantially over the process orifice.

17. The atomising device according to claim 16 wherein the first perforated membrane comprises a nozzle orifice and the second perforated membrane comprises a sieve.

18. The atomising device according to claim 16 wherein the supporting structure comprises an inlet in fluid communication with the second perforated membrane.

19. The atomising device according to claim 16 wherein the surface of the supporting structure is made from plastic.

20. The atomising device according to claim 16 wherein the support element is attached to the surface of the supporting structure by direct bonding or gluing.

21. The atomising device according to claim 20 wherein the support element is attached to the surface of the supporting structure by heating at least part of the support element in order to temporarily melt at least part of the surface of the supporting structure thereby adhering the surface of the supporting structure to the support element.

22. An inhaler comprising
a container for containing a fluid and a pressurised gas;
an atomising device according to claim 16; and
a valve for enabling the fluid to flow from the container to the atomising device,
wherein an atomising body of the atomising device in use operates as a nozzle for spraying the fluid.

23. An inhaler comprising
a container for containing a fluid;
an atomising device according to claim 16; and
a passage enabling the fluid to flow from the container to the atomising device;
wherein an atomising body of the atomising device in use operates as a nozzle for spraying the fluid and wherein, in use, a user action upon the container enables a volume of the container containing the fluid to be reduced, thereby providing a dose of fluid to a user.

24. The inhaler according to claim 23 wherein the dose provided is proportional to the user action.

25. The inhaler according to claim 23 wherein the volume is adjustable by the user action in a continuous manner.

26. The inhaler according to claim 25 wherein the container comprises a syringe for, in use, containing the fluid.

* * * * *